(12) United States Patent
Schär et al.

(10) Patent No.: US 7,303,583 B1
(45) Date of Patent: Dec. 4, 2007

(54) INTERVERTEBRAL IMPLANT

(75) Inventors: Manuel Schär, Muttenz (CH); Jérôme Bernhard, Zürich (CH); Konrad Tagwerker, Basel (CH)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 10/240,525

(22) PCT Filed: Aug. 27, 1999

(86) PCT No.: PCT/EP99/06332

§ 371 (c)(1),
(2), (4) Date: Sep. 30, 2002

(87) PCT Pub. No.: WO01/15637

PCT Pub. Date: Mar. 8, 2001

(51) Int. Cl.
*A61F 2/44* (2006.01)

(52) U.S. Cl. .................................... 623/17.16

(58) Field of Classification Search ............. 623/17.16, 623/17.11, 23.5, 23.58, 23.61, 926; 606/61
See application file for complete search history.

(56) References Cited

U.S. PATENT DOCUMENTS

| | | | |
|---|---|---|---|
| 4,904,261 A | 2/1990 | Dove et al. | |
| 4,960,818 A | 10/1990 | Reilly et al. | 524/440 |
| 5,192,327 A | 3/1993 | Brantigan | 623/17 |
| 5,397,364 A * | 3/1995 | Kozak et al. | 623/17.11 |
| 5,609,636 A * | 3/1997 | Kohrs et al. | 623/17.16 |
| 5,645,598 A * | 7/1997 | Brosnahan, III | 606/61 |
| 5,669,909 A * | 9/1997 | Zdeblick et al. | 606/61 |
| 5,676,146 A * | 10/1997 | Scarborough | 600/431 |
| 5,713,899 A | 2/1998 | Marnay et al. | 606/61 |
| 5,749,916 A * | 5/1998 | Richelsoph | 623/17.16 |
| D397,439 S * | 8/1998 | Koros et al. | D24/155 |
| 5,865,845 A * | 2/1999 | Thalgott | 623/17.16 |
| 5,888,227 A * | 3/1999 | Cottle | 623/17.16 |
| 5,972,368 A * | 10/1999 | McKay | 424/423 |
| 6,096,080 A * | 8/2000 | Nicholson et al. | 623/17.16 |
| 6,143,033 A * | 11/2000 | Paul et al. | 623/17.11 |
| 6,482,233 B1 * | 11/2002 | Aebi et al. | 623/17.11 |
| 6,511,509 B1 * | 1/2003 | Ford et al. | 623/23.5 |

FOREIGN PATENT DOCUMENTS

| | | |
|---|---|---|
| DE | 196 15 938 A1 | 10/1996 |
| FR | 2 724 312 | 3/1996 |
| FR | 2 733 413 | 10/1996 |

* cited by examiner

*Primary Examiner*—Eduardo G. Robert
*Assistant Examiner*—David Comstock
(74) *Attorney, Agent, or Firm*—Stroock & Stroock & Lavan LLP

(57) ABSTRACT

An intervertebral implant is shaped in the form of a hollow cylinder and has a cover face, a base face, a hollow cylinder wall with an outer lateral area and an inner lateral area, as well as a hollow cylinder central axis. The implant is formed at least 95 percent by volume of a radiolucent material which has a modulus of elasticity of between 1 and 20 GPa. Postsurgical observation is permitted by means of X-rays, and at the same time the implant has a high degree of biocompatibility.

28 Claims, 2 Drawing Sheets

INTERVERTEBRAL IMPLANT

FIELD OF THE INVENTION

The invention relates to an intervertebral implant.

BACKGROUND OF THE INVENTION

An intervertebral implant of this type made of an elongate metal plate and therefore opaque to X-rays is known from DE-A 196,15,938. The disadvantages of this known implant reside in its radiopacity which makes a post-surgical assessment of the fusion of the vertebral bodies impossible.

The invention relates to an intervertebral implant which permits a postsurgical observation by means of X-rays and which at the same time is characterised by a high degree of biocompatibility.

The invention further relates to a device in which the relatively low modulus of elasticity of the radiolucent material is apt to encourage an optimum bone growth.

Suitable radiolucent materials include for example polyetheretherketones (PEEK), ultra-high molecular weight polyethylenes (UHMWPE) or polysulfones (PSU), in particular those having a modulus of elasticity of between 3 and 5 GPa.

SUMMARY OF THE INVENTION

According to a preferred exemplary embodiment of the invention, the intervertebral implant is provided with at least one marker made of a radiopaque material which makes up at most 5 percent by volume of the intervertebral implant. This permits the position of the implant to be determined with an X-ray photograph, despite the growth of new bone. The markers preferably consist of titanium or tantalum and are shaped in the form of small pegs or balls.

According to a preferred exemplary embodiment of the invention, the cover face and the base face are each provided with a three-dimensionally structured surface, preferably in a regular arrangement, for example in the form of teeth arranged over a segment of a circle.

Preferably, the cover face and the base face are in a wedge-shaped arrangement relative to each other, forming an angle of, for example, between 10 and 20 degrees.

According to a preferred exemplary embodiment of the invention, the cover face and/or the base face may be provided with one or several guide notches which are oriented towards the hollow cylinder axis. The guide notches are preferably arranged at an angle of 45 degrees±15 degrees as seen from the hollow cylinder axis.

The ratio CF/FCA between the cover face CF and the free cross-sectional area FCA of the hollow cylinder defined by the internal lateral area should suitably be in a range of between 0.5 and 1.6.

According to another preferred exemplary embodiment of the invention, the hollow cylinder wall has a recess directed towards the hollow cylinder axis and extending from the cover face to the base face. On its higher side, the hollow cylinder wall preferably has a separating slot extending parallel to the hollow cylinder axis and reaching from the cover face to the base face, so as to give a U-shaped form to the implant. Preferably, the recess is arranged on the side of the hollow cylinder wall situated opposite to the separating slot as seen from the hollow cylinder axis.

The posterior recess allows the implant to be optimally seated on the end plate of the vertebral body. Thus, it is possible to achieve a high degree of primary stability. The register accuracy thus attained assists in preventing the implant from becoming laterally displaced.

The separating slot encourages the bone onlay on the end plates of the vertebral bodies to grow as rapidly as possible into the implant from the anterior side. In addition, the separating slot allows the implant to be filled in situ (e.g. with bone chips). Preferably, the separating slot has a width of between 6 and 10 mm.

According to a further preferred exemplary embodiment of the invention, the outer lateral area is provided with one or several retaining notches extending at a right angle to the hollow cylinder axis and located equidistant from the cover face and the base face. Preferably, several retaining notches are included which are offset by an amount of 90 degrees and/or 240 degrees as seen from the recess. It is particularly advantageous to provide two further retaining notches which are offset by 180 degrees and lead to the separating slot.

According to a further preferred exemplary embodiment of the invention, the hollow cylinder wall is provided with perforations which may be shaped, for example, in the form of circular bores, slots, or elongate holes. The perforations should be arranged at angles of 0 degrees, 90 degrees and/or 240 degrees, as seen from the recess.

For applications in the region of the lumbar column, the intervertebral implant preferably has a height of between 12 and 23 mm; for applications in the cervical spine, a height of between 4.5 and 12.5 mm is preferred.

With implants designed to be applied in the lumbar column, the outer lateral area preferably extends at a maximum distance of between 14 and 18 mm, measured from the hollow cylinder central axis.

With implants designed to be applied in the cervical spine, the outside lateral area preferably extends at a maximum distance of between 5.5 and 9.5 mm, measured from the hollow cylinder central axis.

BRIEF DESCRIPTION OF THE DRAWINGS

In the following, the invention and exemplary embodiments of the invention will be illustrated in greater detail with reference to the partially diagrammatic representations of one embodiment.

DETAILED DESCRIPTION OF THE INVENTION

Figure 1:
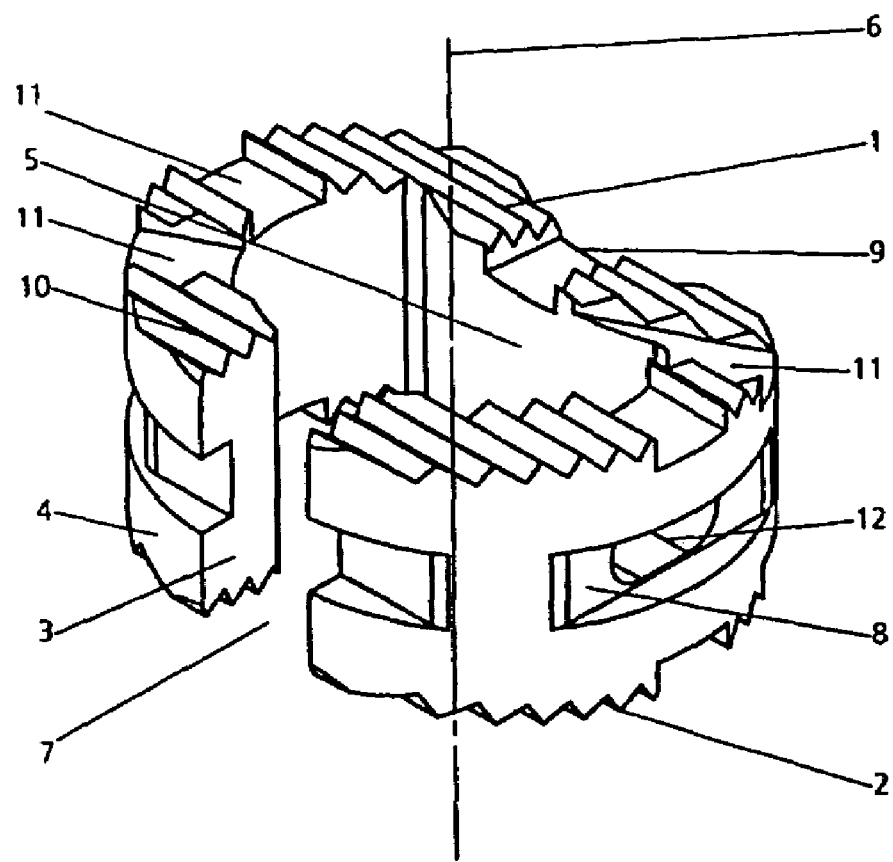
FIG. 1 shows a perspective view of an exemplary preferred embodiment of an intervertebral implant according to the present invention.
Figure 2:
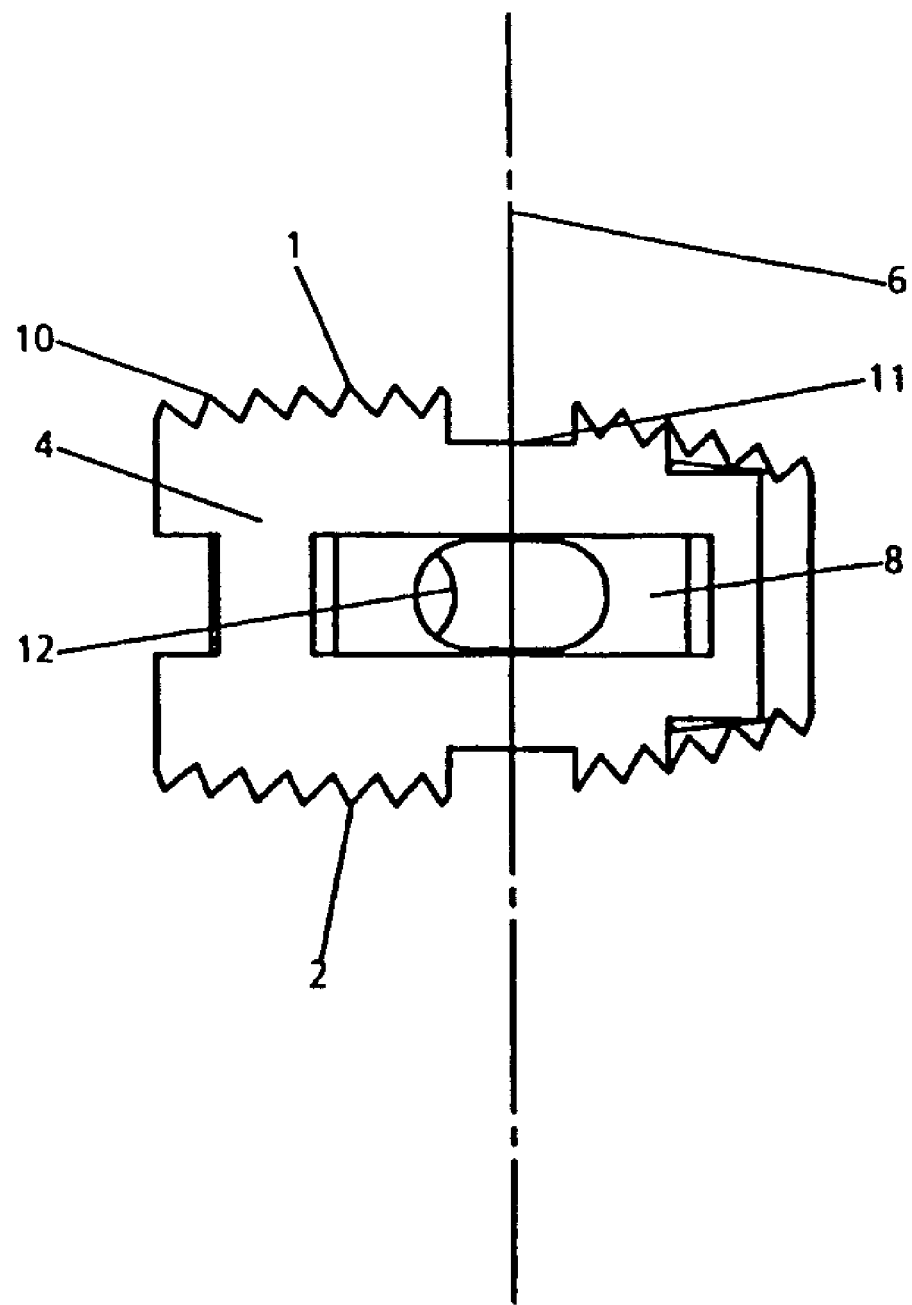
FIG. 2 shows a side view of the intervertebral implant of FIG. 1.

The intervertebral implant shown in FIGS. 1 and 2 is shaped in the form of a hollow cylinder. It has a first cover face 1, a second base face 2, a hollow cylinder wall 3 including an outer lateral area 4 and an inner lateral area 5, as well as a hollow cylinder central axis 6.

The implant is formed at least 95 percent by volume of a radiolucent material such as PEEK (group of polyaryletherketones). Such a material must have a modulus of elasticity of between 1 and 20 GPa. Preferably, the modulus of elasticity is between 3 and 5 GPa.

The intervertebral implant further includes three markers (not shown in the drawings) made of a radiopaque material (tantalum or titanium) which together form at most 5 percent by volume of said intervertebral implant. The total volume (100 percent) is to be understood as the volume occupied by the material of the intervertebral implant, excluding the hollow space enclosed by the implant.

The cover face 1 and the base face 2 of the implant are provided with a three-dimensionally structured surface 10 which includes teeth regularly arranged over a segment of a circle. The arrangement of the teeth of the implant in the form of a segment of a circle—combined with the wedge-shaped form of the implant—confers a curvature to the cover face and the base face, which in turn allows the implant to be optimally seated on the end plate of the vertebral body.

As may be seen in FIG. 2, the cover face 1 and the base face 2 are arranged in a wedge-shaped form relative to each other, forming approximately an angle of between 10 and 20 degrees.

On the cover face 1 and the base face 2, the implant is provided with several lateral and antero-lateral guide notches 11 which are oriented towards the hollow cylinder axis 6. The guide notches serve for inserting the implant, by means of the blades of a distraction apparatus, into the intervertebral space thus spread apart. The offset arrangement of the notch pairs permits a lateral, an antero-lateral, and an anterior insertion of the implant.

The guide notches 11 are angularly offset by 45 degrees±15 degrees as seen from the hollow cylinder axis 6.

As may be seen in FIG. 1, the hollow cylinder wall 3 is provided with a posterior recess 9 oriented towards the hollow cylinder axis 6 and extending from the cover face 1 to the base face 2. On its higher (anterior) side, the hollow cylinder wall 3 has a separating through-slot 7 extending parallel to the hollow cylinder axis 6 and reaching from the cover face 1 to the base face 2 at the maximum height defined between the cylinder faces 1 and 2, so as to give a U-shaped form to the implant. The recess 9 is arranged on the side of the hollow cylinder wall 3 located opposite to the separating slot 7 as seen from the hollow cylinder axis 6.

The outer lateral area 4 is provided with two lateral retaining notches 8 extending at a right angle to the hollow cylinder axis 6, and thus in a plane perpendicular to axis 6, and located equidistant from the cover face 1 and the base face 2. The retaining notches 8 are angularly offset by an amount of 90 degrees and 240 degrees as seen from the recess 9.

Furthermore, two additional, anterior retaining notches 8 are included which are offset by an amount of 180 degrees and lead to the separating slot 7.

The function of the retaining notches, on the one hand, is to avoid an axial displacement of the implant holding device and, on the other hand, is to provide a plane contact surface for this instrument.

The hollow cylinder wall 3 is provided with at least one oval perforation 12 which is offset by an amount of 90 degrees as seen from the recess 9.

The invention claimed is:

1. An intervertebral implant consisting:
   a first face for engaging a first vertebral endplate and a second face for engaging a second vertebral endplate, outer and inner walls extending between the faces, a central axis, an opening defined by the inner wall, a through-slot extending from the first face through to the second face and from the outer wall through to the inner wall, the through-slot aligned with the central axis;
   wherein at least 95 percent by volume of the implant is formed of a radiolucent material with a modulus of elasticity between 1 GPa and 20 GPa;
   wherein the first face and the second face each have a plurality of three-dimensional projections extending therefrom;
   wherein at least one of the first and second faces is provided with at least one guide notch and the second face contains a perforation, the perforation not aligned with the central axis; and
   wherein at least a portion of the implant is formed of a metallic, radiopaque material.

2. The intervertebral implant of claim 1 wherein the modulus of elasticity of the radiolucent material is between 3 GPa and 5 GPa.

3. The intervertebral implant of claim 1, wherein the implant further comprises at least one marker formed of a radiopaque material.

4. The intervertebral implant of claim 3, wherein at least one marker is no greater than 5 percent by volume of said intervertebral implant.

5. The intervertebral implant of claim 1, wherein a portion of the three-dimensional projections forms a grooved surface.

6. The intervertebral implant of claim 1, wherein at least a portion of the three-dimensional projections comprises teeth.

7. The intervertebral implant of claim 6, wherein the teeth are arranged in a regular pattern.

8. The intervertebral implant of claim 1, wherein at least a portion of the three-dimensional projections comprises a generally arcuate arrangement of teeth.

9. The intervertebral implant of claim 1, wherein the first and second faces are disposed transverse to each so that the cylinder has a wedge-shaped, tapered form.

10. The intervertebral implant of claim 9, wherein the first and second faces are disposed at an angle of between 10° and 20° with respect to each other.

11. The intervertebral implant of claim 1, wherein the radiolucent material is polyaryletherketone.

12. The intervertebral implant of claim 1, wherein at least one guide notch is disposed at an angle of between 30° and 60° with respect to the central axis.

13. The intervertebral implant of claim 1, wherein the ratio of the area of the first face and the free cross-sectional area of the opening defined by the inner wall is between 0.5 and 1.6.

14. The intervertebral implant of claim 1, wherein the outer wall is provided with at least one recess aligned with the central axis and extending between the first and second faces.

15. The intervertebral implant of claim 14, wherein the implant has a generally U-shaped form.

16. The intervertebral implant of claim 14, wherein the recess is aligned with the through-slot.

17. The intervertebral implant of claim 1, wherein the through-slot has a through-slot height defined between the first and second faces and the implant has a maximum height defined between the first and second faces, wherein the through-slot height is about the same as the maximum height of the implant.

18. The intervertebral implant of claim 1, wherein the outer wall comprises at least one retaining notch intersecting the through-slot.

19. The intervertebral implant of claim 1, wherein the outer wall comprises at least one retaining notch extending in a plane perpendicular to the central axis.

20. The intervertebral implant of claim 19, wherein the retaining notch is disposed equidistant from the first and second faces.

21. The intervertebral implant of claim 1, wherein the outer wall is provided with at least one perforation.

22. The intervertebral implant of claim 21, wherein at least one perforation has a shape selected from the group consisting of circular bores, slots, or elongate holes.

23. The intervertebral implant of claim 22, wherein at least one of the at least one perforation intersects a recess in the outer wall that is aligned with the central axis and extends between the first and second faces.

24. The intervertebral implant of claim 1, wherein the implant has a height between 12 and 23 mm.

25. The intervertebral implant of claim 1, wherein the implant has a height between 4.5 mm and 12.5 mm.

26. The intervertebral implant of claim 1, wherein the outer wall is disposed at a maximum distance of between 14 mm and 18 mm from the central axis.

27. The intervertebral implant of claim 1, wherein the outer wall is disposed at a maximum distance of between 5.5 mm and 9.5 mm from the central axis.

28. The intervertebral implant of claim 1, wherein the radiolucent material is selected from the group consisting of polyetheretherketones, ultra-high molecular weight polyethylenes, and polysulfones.

* * * * *